United States Patent [19]

Irikura

[11] 3,962,249
[45] June 8, 1976

[54] 1-(3-PHENYLPROPYL)-4-FUROYLPIPERAZINE DERIVATIVES

[75] Inventor: Tsutomu Irikura, Tokyo, Japan

[73] Assignee: Kyorin Seiyaku Kabushiki Kaisha, Tokyo, Japan

[22] Filed: Mar. 6, 1975

[21] Appl. No.: 555,992

[30] Foreign Application Priority Data
Mar. 6, 1974 Japan.............................. 49-26067
Sept. 26, 1974 Japan............................ 49-110709

[52] U.S. Cl.............................. 260/268 C; 424/250
[51] Int. Cl.².............. C07D 405/02; C07D 405/06
[58] Field of Search................................ 260/268 C

[56] References Cited
OTHER PUBLICATIONS
Soeder, Alfons, Chemical Abstracts, vol. 79, 42553u, (1973).

Primary Examiner—Alton D. Rollins
Assistant Examiner—Jose Tovar
Attorney, Agent, or Firm—Wenderoth, Lind & Ponack

[57] ABSTRACT 1-(3-Phenylpropyl)-4-furoylpiperazine represented by the following general formula (I),

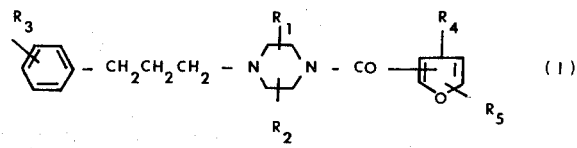

(wherein: $R_1$ and $R_2$, which may be the same or different, each represents a hydrogen atom or a lower alkyl group containing 1 to 4 carbon atoms; $R_3$ represents a hydrogen atom, a halogen atom, a lower alkyl group containing 1 to 4 carbon atoms, or a lower alkoxy groups containing 1 to 4 carbon atoms; $R_4$ and $R_5$, which may be the same or different, each represents a hydrogen atom or a lower alkyl group containing 1 to 4 carbon atoms), and pharmaceutically acceptable addition salts thereof.

28 Claims, No Drawings

1-(3-PHENYLPROPYL)-4-FUROYLPIPERAZINE DERIVATIVES

This invention relates to 1-(3-phenylpropyl)-4-furoylpiperazines represented by the following general formula (I):

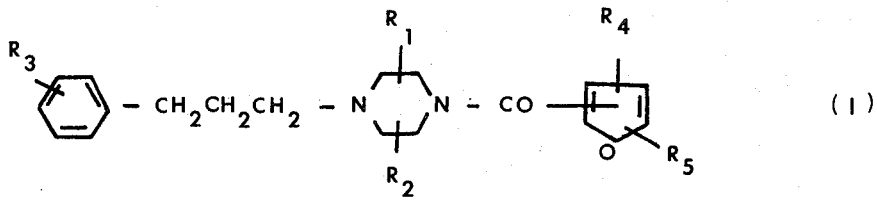

(wherein: $R_1$ and $R_2$, which may be the same or different, each represents a hydrogen atom or a lower alkyl group containing 1 to 4 carbon atoms; $R_3$ represents a hydrogen atom, a halogen atom, a lower alkyl group containing 1 to 4 carbon atoms, or a lower alkoxy group containing 1 to 4 carbon atoms; $R^4$ and $R^5$, which may be the same or different, each represents a hydrogen atom or a lower alkyl group containing 1 to 4 carbon atoms), and pharmaceutically acceptable addition salts thereof.

It is an object of this invention to provide the new 1-(3-phenylpropyl)-4-furoylpiperazines and pharmaceutically acceptable acid addition salts thereof. Other objects of this invention will be apparent to those skilled in the art to which this invention pertains.

The new compounds of this invention, 1-(3-phenylpropyl)-4-furoylpiperazines and pharmaceutically acceptable acid addition salts thereof are useful as an analgesic agent, and characterized by their ability to produce analgesia without such side effects as seen in narcotic analgesics.

The new compounds of this invention may readily be prepared by methods known to the art. The following equation illustrates the preparation of the new compounds of this invention:

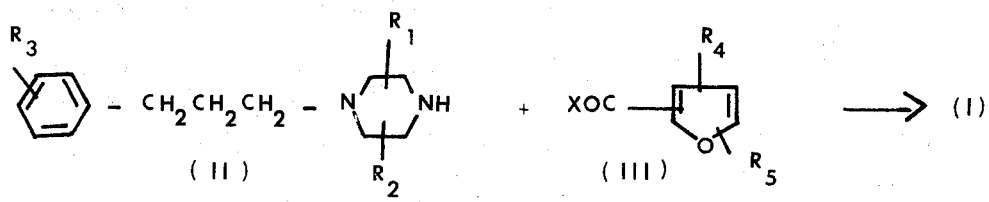

(wherein: $R_1$, $R_2$, $R_3$, $R_4$ and $R_5$ are as defined hereinbefore, and X is a halogen atom).

Referring to the equation, it will be seen that 1-(3-phenylpropyl)piperazines (II) are reacted with furancarboxylic acids halogenide (III) to form 1-(3-phenylpropyl)-4-furoylpiperazines (I).

1-(3-Phenylpropyl)piperazines (II) may be prepared by the reaction of 3-phenylpropylbromides or 1-p-toluenesulfonyloxy-3-phenylpropanes and piperazines, by the hydrogenating reaction of 1-(3-phenylpropionyl)-3-oxopiperazines, 1-(3-phenylpropyl)-2,6-dioxo-piperazines or 1-(3-phenylpropyl)-4-benzyl piperazines, or by the hydrolyzing reaction of 1-(3-phenylpropyl)-4-acyl or alkoxycarbonyl piperazines.

As is evident from the structural formula of the compounds of this invention, 1-(3-phenylpropyl)-4-furoylpiperazines contain a basic nitrogen atom, which can react with acids to form acid addition salts. Such salts are readily prepared by the action of stoichiometrically equivalent amounts of the desired base and a selected acid in a mutual solvent.

Examples of acids which are suitable for the preparation of acid addition salts are inorganic acids, such as, for example, hydrochloric, hydrobromic, sulfuric, nitric, phosphoric and the like acids; and organic acids, such as, for example, acetic, propionic, lactic, benzoic, maleic, salicylic, citric and the like acids. Preferable, pharmaceutically useful acids are used.

Some of the new compounds of this invention possess one or two centers of asymmetry, and therefore occur in diastereoisomeric forms.

The analgesic effect and toxcity of some of this invention are given in Table 1. These compounds showed high analgesic potency in mice when determined their effect by the inhibition of acetic acid-induced writhing counts.

The anti-writhing effects of these compounds were not antagonized at all by a narcotic antagonist, levallorphan. Furthermore, these compounds caused non respiratory depression in rabbits, which was one of the special feature of the pharmacological effects of narcotic analgesics, by intravenous injection of 10 mg/kg or more.

Thus, it is considered that the compounds of this invention have non narcotic properties with high degree of analgesic potency and being placed under the category of non-narcotic analgesic agents.

The usual forms of therapeutic administration for the compounds of this invention may be employed as follows. For example, the compound of Example 2 may be composited with a suitable pharmaceutical carrier to provide solutions, syrups, tablets, capsules, dragees, powders, or the like. The dosage unit form may contain from about 20 to about 80 mg of the active substance. For example, in the case solutions for injection, the ampoule may contain a 0.5 to 2% solution with 20 to 50 mg of active substance per ampoule. In the case of tablets or the like the dosage of active substance may be 50 to 80 mg.

Table 1

| Example No. | $ED_{50}$ *) (mg/kg) | $LD_{50}$ **) (mg/kg) |
| --- | --- | --- |
| 1 | 7.80 | 400 |
| 2 | 1.52 | >500 |
| 3 | 5.17 | 300 |
| 4 | 3.42 | >750 |
| 5 | 2.20 | >500 |
| 7 | 3.00 | 400 |
| 8 | 3.35 | 350 |

Table 1-continued

| Example No. | ED₅₀ *) (mg/kg) | LD₅₀ **) (mg/kg) |
|---|---|---|
| 9 | 8.85 | 400 |
| 11 | 1.81 | 170 |
| 12 | 3.93 | 200 |
| 15 | 1.00 | >750 |
| 16 | 1.05 | >500 |

*) 50% Effective dose.
**) LD$_{50}$ in mice by subcutaneous injection of the drugs (calculated by the Up and Down method). Drugs are dissolved in physiological saline prior to injection.

The following examples more specifically illustrate the preparation of the new compounds of this invention and their salts.

EXAMPLE 1

1-(3-Phenylpropyl)-4-(2-furoyl)piperazine hydrochloride

2-Furoyl chloride (69 g) was added dropwise to a solution of 1-(3-phenylpropyl)piperazine (95 g) and benzene (1 l) with stirring and then the stirring was continued at room temperature for 1 hour.

An aqueous NaOH solution was added to the reaction mixture, which was stirred at room temperature for thirty minutes. The benzene layer was separated, washed with $H_2O$ and extracted with an aqueous HCl solution. The extracts were neutralized with an aqueous NaOH solution and extracted with benzene. The benzene layer was washed with $H_2O$, dried over anhydrous $Na_2SO_4$ and evaporated to an oily residue. The oily residue was dissolved in acetone and treated with alcoholic hydrogen chloride to crystallize.

Recrystallization from isopropanol-acetone yielded 125 g (79%) of colorless needles, melting point, 191° – 194°C.

| Analysis for $C_{18}H_{22}N_2O_2$.HCl | C | H | N |
|---|---|---|---|
| Calcd. | 64.59 | 6.92 | 8.37 |
| Found | 64.69 | 7.06 | 8.24 |

EXAMPLE 2 trans-1-(3-Phenylpropyl)-2,5-dimethyl-4-(2-furoyl)-piperazine hydrochloride

2-Furoyl chloride (13 g) was added dropwise to a solution of trans-1-(3-phenylpropyl)-2,5-dimethylpiperazine [b.p. 138 – 140 (4 mmHg), dipicrate, m.p. 258° – 261°C] (21 g) and benzene (200 ml).

After the addition was complete, the stirring was continued for 1 hour. The precipitate formed was separated and washed well with benzene.

Recrystallization from acetone yielded 18 g (86%) of colorless needles, melting point, 142° – 145°C.

| Analysis for $C_{20}H_{26}N_2O_2$.HCl | C | H | N |
|---|---|---|---|
| Calcd. | 66.19 | 7.50 | 7.72 |
| Found | 66.05 | 7.47 | 7.70 |

EXAMPLE 3

1-(3-Phenylpropyl)-2-methyl-4-(2-furoyl)piperazine

2-Furoyl chloride (1.5 g) was added dropwise with stirring to a solution of 1-(3-phenylpropyl)-2-methylpiperazine [b.p. 138° – 140°C (8 mmHg)] (2.2 g) and $CHCl_3$ (100 ml).

The reaction mixture was stirred at room temperature for one hour. The organic layer was washed well with an aqueous NaOH solution and $H_2O$, dried over anhydrous $Na_2SO_4$ and evaporated to obtain an oily residue. The oily residue was purified over alumina with benzene to afford 2.3 g (75%) of a colorless oil.

| Analysis for $C_{19}H_{24}N_2O_2$ | C | H | N |
|---|---|---|---|
| Calcd. | 73.03 | 7.74 | 8.97 |
| Found | 72.85 | 7.86 | 9.01 |

EXAMPLE 4

1-(3-Phenylpropyl)-3-methyl-4-(2-furoyl)piperazine hydrochloride

The compound was obtained by following the same process as in Example 2 from a mixture of 1-(3-phenylpropyl)-3-methylpiperazine [b.p. 120° – 125°C (3 mmHg), dipicrate, m.p. 249° – 250°C], 2-furoyl chloride and benzene.

Melting point was 145° – 148°C.

| Analysis for $C_{19}H_{24}N_2O_2$.HCl | C | H | N |
|---|---|---|---|
| Calcd. | 65.41 | 7.22 | 8.03 |
| Found | 65.42 | 7.14 | 8.02 |

EXAMPLE 5

1-(3-Phenylpropyl)-3,3-dimethyl-4-(2-furoyl)piperazine hydrochloride

The compound was obtained by following the same process as in Example 2 from a mixture of 1-(3-phenylpropyl)-3,3-dimethylpiperazine [b.p. 111°C (2 mmHg), dipicrate, m.p. 195° – 200°C], 2-furoyl chloride and benzene.

Melting point was 143° – 145°C.

| Analysis for $C_{20}H_{26}N_2O_2$.HCl | C | H | N |
|---|---|---|---|
| Calcd. | 66.19 | 7.50 | 7.72 |
| Found | 66.02 | 7.77 | 7.66 |

EXAMPLE 6

1-[3-(p-Methoxyphenyl)propyl]-4-(2-furoyl)piperazine hydrochloride

The compound was obtained by following the same process as in Example 2 from a mixture of 1-[3-(m-methoxyphenyl)propyl]piperazine [b.p. 138° – 140°C (2 mmHg), dihydrochloride, m.p. 221° – 225°C], 2-furoyl chloride and benzene.

Melting point, 180° – 185°C.

Analysis for $C_{19}H_{24}N_2O_3 \cdot HCl$

|  | C | H | N |
|---|---|---|---|
| Calcd. | 62.54 | 6.91 | 7.68 |
| Found | 62.41 | 6.96 | 7.84 |

EXAMPLE 7

1-[3-(o-Methylphenyl)propyl]-4-(2-furoyl)piperazine hydrochloride

The compound was obtained by following the same process as in Example 2 from a mixture of 1-[3-(o-methylphenyl)propyl]piperazine [b.p. 135° – 136°C (2 mmHg), dihydrochloride, m.p. 240° – 245°C], 2-furoyl chloride and benzene.

Melting point, 183° – 187°C.

Analysis for $C_{19}H_{24}N_2O_2 \cdot HCl$

|  | C | H | N |
|---|---|---|---|
| Calcd. | 65.41 | 7.22 | 8.03 |
| Found | 65.58 | 7.20 | 8.11 |

EXAMPLE 8

1-[3-(m-Methylphenyl)propyl]-4-(2-furoyl)piperazine hydrochloride

The compound was obtained by following the same process as in Example 1 from a mixture of 1-[3-(m-methylphenyl)propyl]piperazine [b.p. 137° – 145°C (2 mmHg), dihydrochloride, m.p. 237°C], 2-furoyl chloride and benzene.

Melting point, 170° – 174°C.

Analysis for $C_{19}H_{24}N_2O_2 \cdot HCl$

|  | C | H | N |
|---|---|---|---|
| Calcd. | 65.41 | 7.22 | 8.03 |
| Found | 65.44 | 6.95 | 8.22 |

EXAMPLE 9

1-[3-(p-Ethoxyphenyl)propyl]-4-(2-furoyl)piperazine hydrochloride

The compound was obtained by following the same process as in Example 2 from a mixture of 1-[3-(p-ethoxyphenyl)propyl]piperazine [b.p. 162° – 165°C (4 mmHg), dihydrochloride, m.p. 232° – 239°C], 2-furoyl chloride and benzene.

Melting point, 190° – 196°C.

Analysis for $C_{20}H_{26}N_2O_3 \cdot HCl$

|  | C | H | N |
|---|---|---|---|
| Calcd. | 63.40 | 7.18 | 7.39 |
| Found | 63.19 | 7.16 | 7.33 |

EXAMPLE 10

1-(3-Phenylpropyl)-4-(5-methyl-2-furoyl)piperazine hydrochloride

The compound was obtained by following the same process as in Example 1 from a mixture of 1-(3-phenylpropyl)piperazine, 5-methyl-2-furoyl chloride and benzene.

Melting point was 174° – 178°C.

Analysis for $C_{19}H_{24}N_2O_2 \cdot HCl$

|  | C | H | N |
|---|---|---|---|
| Calcd. | 65.41 | 7.22 | 8.03 |
| Found | 65.67 | 7.03 | 8.05 |

EXAMPLE 11

1-(3-Phenylpropyl)-4-(2-methyl-3-furoyl)piperazine hydrochloride

The compound was obtained by following the same process as in Example 1 from a mixture of 1-(3-phenylpropyl)piperazine, 2-methyl-3-furoyl chloride and benzene.

Melting point was 185° – 189°C.

Analysis for $C_{19}H_{24}N_2O_2 \cdot HCl$

|  | C | H | N |
|---|---|---|---|
| Calcd. | 65.41 | 7.22 | 8.03 |
| Found | 65.35 | 7.29 | 8.15 |

EXAMPLE 12

1-(3-Phenylpropyl)-4-(5-methyl-3-furoyl)piperazine hydrochloride

The compound was obtained by following the same process as in Example 1 from a mixture of 1-(3-phenylpropyl)piperazine, 5-methyl-2-furoyl chloride and benzene.

Melting point was 203° – 207°C.

Analysis for $C_{19}H_{24}N_2O_2 \cdot HCl$

|  | C | H | N |
|---|---|---|---|
| Calcd. | 65.41 | 7.22 | 8.03 |
| Found | 65.25 | 7.12 | 8.09 |

EXAMPLE 13

1-(3-Phenylpropyl)-4-(2,5-dimethyl-3-furoyl)piperazine hydrochloride

The compound was obtained by following the same process as in Example 1 from a mixture of 1-(3-phenylpropyl)piperazine, 2,5-dimethyl-3-furoyl chloride and benzene.

Melting point was 228° – 232°C.

Analysis for $C_{20}H_{28}N_2O_2 \cdot HCl$

|  | C | H | N |
|---|---|---|---|
| Calcd. | 66.19 | 7.50 | 7.72 |
| Found | 66.33 | 7.49 | 7.96 |

EXAMPLE 14 cis-1-(3-Phenylpropyl)-2,3-dimethyl-4-(2-furoyl)piperazine hydrochloride

The compound was obtained by following the same process as in Example 1 from a mixture of cis-1-(3- phenylpropyl)-2,3-dimethylpiperazine [b.p. 126° – 128°C (2 mmHg), dipicrate, m.p. 227° – 228°C], 2-furoyl chloride and benzene.

Melting point was 160° – 162°C.

Analysis for $C_{20}H_{26}N_2O_2.HCl$

|  | C | H | N |
| --- | --- | --- | --- |
| Calcd. | 66.19 | 7.50 | 7.72 |
| Found | 66.19 | 7.57 | 7.74 |

EXAMPLE 15 trans-1-[3-(o-Methylphenyl)propyl]-2,5-dimethyl-4-(2-furoyl)piperazine hydrochloride The compound was obtained by following the same process as in Example 2 from a mixture of trans-1-[3-(o-methylphenyl)propyl]-2,5-dimethylpiperazine [b.p. 130° – 140°C (4 mmHg), dipicrate, 250° – 252°C], 2-furoyl chloride and benzene.

Melting point was 158° – 163°C.

Analysis for $C_{21}H_{28}N_2O_2.HCl$

|  | C | H | N |
| --- | --- | --- | --- |
| Calcd. | 66.92 | 7.76 | 7.43 |
| Found | 67.21 | 7.98 | 7.44 |

EXAMPLE 16 trans-1-[3-(m-Methylphenyl)propyl]-2,5-dimethyl-4-(2-furoyl)piperazine hydrochloride The compound was obtained by following the same process as in Example 2 from a mixture of trans-1-[3-(m-methylphenyl)propyl]-2,5-dimethylpiperazine [b.p. 125° – 132°C (4 mmHg), dipicrate, m.p. 245° – 248°C], 2-furoyl chloride and benzene.

Melting point was 184° – 187°C.

Analysis for $C_{21}H_{28}N_2O_2.HCl$

|  | C | H | N |
| --- | --- | --- | --- |
| Calcd. | 66.92 | 7.76 | 7.43 |
| Found | 66.67 | 7.99 | 7.28 |

EXAMPLE 17 trans-1-(3-Phenylpropyl)-2,3-dimethyl-4-(2-furoyl)-piperazine

The compound was obtained by following the same process as in Example 3 from a mixture of trans-1-(3-phenylpropyl)-2,3-dimethylpiperazine [b.p. 130° – 132°C (2 mmHg), dipicrate, m.p. 195° – 196°C], 2-furoyl chloride and benzene.

Analysis for $C_{20}H_{26}N_2O_2.HCl$

|  | C | H | N |
| --- | --- | --- | --- |
| Calcd. | 73.59 | 8.03 | 8.58 |
| Found | 73.75 | 8.31 | 8.45 |

EXAMPLE 18 trans-1-[3-(o-Methoxyphenyl)propyl]-2,5-dimethyl-4-(2-furoyl)piperazine hydrochloride The compound was obtained by following the same process as in Example 2 from a mixture of trans-1-[3-(o-methoxyphenyl)propyl]-2,5-dimethylpiperazine [b.p. 146° – 150°C (2 mmHg), dipicrate, m.p. 260° – 265°C], 2-furoyl chloride and benzene.

Melting point was 173° –175°C.

Analysis for $C_{21}H_{28}N_2O_3.HCl$

|  | C | H | N |
| --- | --- | --- | --- |
| Calcd. | 64.19 | 7.44 | 7.13 |
| Found | 64.13 | 7.45 | 6.96 |

EXAMPLE 19

1-[3-(o-Methylphenyl)propyl]-3-methyl-4-(2-furoyl)-piperazine hydrochloride

The compound was obtained by following the same process as in Example 2 from a mixture of 1-[3-(o-methylphenyl)propyl]-3-methylpiperazine [b.p. 120° – 125°C (2 mmHg), dipicrate, m.p. 245° – 250°C], 2-furoyl chloride and benzene.

Melting point was 142° – 145°C.

Analysis for $C_{20}H_{26}N_2O_2.HCl$

|  | C | H | N |
| --- | --- | --- | --- |
| Calcd. | 66.19 | 7.50 | 7.72 |
| Found | 66.09 | 7.51 | 7.62 |

EXAMPLE 20 trans-1-(3-Phenylpropyl)-2,5-dimethyl-4-(5-methyl-3-furoyl)piperazine hydrochloride The compound was obtained by following the same process as in Example 2 from a mixture of trans-1-(3-phenylpropyl)-2,5-dimethylpiperazine, 5-methyl-3-furoyl chloride and benzene.

Melting point was 180° – 185°C.

Analysis for $C_{21}H_{28}N_2O_2.HCl$

|  | C | H | N |
| --- | --- | --- | --- |
| Calcd. | 66.92 | 7.76 | 7.43 |
| Found | 67.02 | 7.75 | 7.30 |

EXAMPLE 21 trans-1-[3-(o-Methylphenyl)propyl]-2,5-dimethyl-4-(5-methyl-3-furoyl)piperazine hydrochloride The compound was obtained by following the same process as in Example 2 from a mixture of trans-1-[3-(o-methylphenyl)propyl]-2,5-dimethylpiperazine, 5-methyl-3-furoyl chloride and benzene.

Melting point was 149° –152°C.

Analysis for $C_{22}H_{30}N_2O_2.HCl$

|  | C | H | N |
| --- | --- | --- | --- |
| Calcd. | 67.59 | 7.99 | 7.17 |

Analysis for $C_{22}H_{30}N_2O_2 \cdot HCl$

|       | C     | H    | N    |
|-------|-------|------|------|
| Found | 67.58 | 8.04 | 7.04 |

EXAMPLE 22 trans-1-(3-Phenylpropyl)-2,5-dimethyl-4-(3-methyl-2-furoyl)piperazine hydrochloride The compound was obtained by following the same process as in Example 2 from a mixture of trans-1-(3-phenylpropyl)-2,5-dimethylpiperazine, 3-methyl-2-furoyl chloride and benzene.

Melting point, 156° – 158°C.

Analysis for $C_{21}H_{28}N_2O_2 \cdot HCl$

|        | C     | H    | N    |
|--------|-------|------|------|
| Calcd. | 66.92 | 7.76 | 7.43 |
| Found  | 67.00 | 7.83 | 7.42 |

EXAMPLE 23 trans-1-(3-Phenylpropyl)-2,5-dimethyl-4-(5-methyl-2-furoyl)piperazine hydrochloride The compound was obtained by following the same process as in Example 2 from a mixture of trans-1-(3-phenylpropyl)-2,5-dimethylpiperazine, 5-methyl-2-furoyl chloride and benzene.

Melting point, 164° – 167°C.

Analysis for $C_{21}H_{28}N_2O_2 \cdot HCl$

|        | C     | H    | N    |
|--------|-------|------|------|
| Calcd. | 66.92 | 7.76 | 7.43 |
| Found  | 66.69 | 7.78 | 7.29 |

EXAMPLE 24 trans-1-(3-Phenylpropyl)-2,5-dimethyl-4-(2-methyl-3-furoyl)piperazine hydrochloride The compound was obtained by following the same process as in Example 2 from a mixture of trans-1-(3-phenylpropyl)-2,5-dimethylpiperazine, 2-methyl-3-furoyl chloride and benzene.

Melting point, 168° – 171°C.

Analysis for $C_{21}H_{28}N_2O_2 \cdot HCl$

|        | C     | H    | N    |
|--------|-------|------|------|
| Calcd. | 66.92 | 7.76 | 7.43 |
| Found  | 66.78 | 7.75 | 7.41 |

EXAMPLE 25

1-(3-Phenylpropyl)-3-methyl-4-(5-methyl-2-furoyl)-piperazine hydrochloride

The compound was obtained by following the same process as in Example 2 from a mixture of 1-(3-phenylpropyl)-3-methylpiperazine, 5-methyl-2-furoyl chloride and benzene.

Melting point was 134° – 136°C.

Analysis for $C_{20}H_{26}N_2O_2 \cdot HCl$

|        | C     | H    | N    |
|--------|-------|------|------|
| Calcd. | 66.19 | 7.50 | 7.72 |
| Found  | 66.25 | 7.61 | 7.56 |

EXAMPLE 26

1-(3-Phenylpropyl)-3-methyl-4-(3-methyl-2-furoyl)-piperazine hydrochloride

The compound was obtained by following the same process as in Example 2 from a mixture of 1-(3-phenylpropyl)-3-methylpiperazine, 3-methyl-2-furoyl chloride and benzene.

Melting point was 148° – 151°C.

Analysis for $C_{20}H_{26}N_2O_2 \cdot HCl$

|        | C     | H    | N    |
|--------|-------|------|------|
| Calcd. | 66.19 | 7.50 | 7.72 |
| Found  | 66.32 | 7.58 | 7.69 |

EXAMPLE 27

1-[3-(o-Methylphenyl)propyl]-3-methyl-4-(3-methyl-2-furoyl)piperazine hydrochloride The compound was obtained by following the same process as in Example 2 from a mixture of 1-[3-(o-methylphenyl)propyl]-3-methylpiperazine, 3-methyl-2-furoyl chloride and benzene.

Melting point was 173° – 176°C.

Analysis for $C_{21}H_{28}N_2O_2 \cdot HCl$

|        | C     | H    | N    |
|--------|-------|------|------|
| Calcd. | 66.92 | 7.76 | 7.43 |
| Found  | 66.70 | 7.84 | 7.33 |

EXAMPLE 28

1-[3-(m-Chlorophenyl)propyl]-4-(2-furoyl)piperazine hydrochloride

The compound was obtained by following the same process as in Example 2 from a mixture of 1-[3-(m-chlorophenyl)propyl]piperazine, 2-furoyl chloride and benzene.

Melting point was 167° – 169°C.

Analysis for $C_{18}H_{21}N_2O_2 \cdot HCl$

|        | C     | H    | N    |
|--------|-------|------|------|
| Calcd. | 58.54 | 6.00 | 7.59 |
| Found  | 58.25 | 6.29 | 7.74 |

What is claimed is:
1. A compound of formula

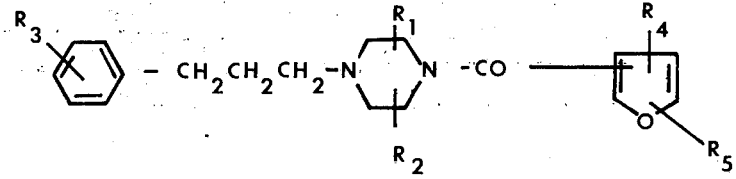

wherein $R_1$ and $R_2$, independently of each other, represent hydrogen or alkyl having 1 to 4 carbon atoms; $R_3$ represents hydrogen, halogen, alkyl having 1 to 4 carbon atoms, or alkoxy having 1 to 4 carbon atoms; $R_4$ and $R_5$ independently of each other, represent hydrogen or alkyl having 1 to 4 carbon atoms, or a pharmaceutically acceptable acid addition salt thereof.

2. The compound according to claim 1, namely 1-(3-Phenylpropyl)-4-(2-furoyl)piperazine hydrochloride.

3. The compound according to claim 1, namely trans-1-(3-Phenylpropyl)-2,5-dimethyl-4-(2-furoyl)piperazine hydrochloride.

4. The compound according to claim 1, namely 1-(3-Phenylpropyl)-2-methyl-4-(2-furoyl)piperazine hydrochloride.

5. The compound according to claim 1, namely 1-(3-Phenylpropyl)-3-methyl-4-(2-furoyl)piperazine hydrochloride.

6. The compound according to claim 1, namely 1-(3-Phenylpropyl)-3,3-dimethyl-4-(2-furoyl)piperazine hydrochloride.

7. The compound according to claim 1, namely 1-[3-(p-Methoxyphenyl)propyl]-4-(2-furoyl)piperazine hydrochloride.

8. The compound according to claim 1, namely 1-[3-(o-Methylphenyl)propyl]-4-(2-furoyl)piperazine hydrochloride.

9. The compound according to claim 1, namely 1-[3-(m-Methylphenyl)propyl]-4-(2-furoyl)piperazine hydrochloride.

10. The compound according to claim 1, namely 1-[3-(p-Ethoxyphenyl)propyl]-4-(2-furoyl)piperazine hydrochloride.

11. The compound according to claim 1, namely 1-(3-Phenylpropyl)-4-(5-methyl-2-furoyl)piperazine hydrochloride.

12. The compound according to claim 1, namely 1-(3-Phenylpropyl)-4-(2-methyl-3-furoyl)piperazine hydrochloride.

13. The compound according to claim 1, namely 1-(3-Phenylpropyl)-4-(5-methyl-3-furoyl)piperazine hydrochloride.

14. The compound according to claim 1, namely 1-(3-Phenylpropyl)-4-(2,5-dimethyl-3-furoyl)piperazine hydrochloride.

15. The compound according to claim 1, namely cis-1-(3-Phenylpropyl)-2,3-dimethyl-4-(2-furoyl)piperazine hydrochloride.

16. The compound according to claim 1, namely trans-1-[3-(o-Methylphenyl)propyl]-2,5-dimethyl-4-(2-furoyl)piperazine hydrochloride.

17. The compound according to claim 1, namely trans-1-[3-(m-Methylphenyl)propyl]-2,5-dimethyl-4-(2-furoyl)piperazine hydrochloride.

18. The compound according to claim 1, namely trans-1-(3-Phenylpropyl)-2,3-dimethyl-4-(2-furoyl)-piperazine hydrochloride.

19. The compound according to claim 1, namely trans-1-[3-(o-Methoxyphenyl)propyl]-2,5-dimethyl-4-(2-furoyl)piperazine hydrochloride.

20. The compound according to claim 1, namely 1-[3-(o-Methylphenyl)propyl]-3-methyl-4-(2-furoyl)-piperazine hydrochloride.

21. The compound according to claim 1, namely trans-1-(3-Phenylpropyl)-2,5-dimethyl-4-(5-methyl-3-furoyl)piperazine hydrochloride.

22. The compound according to claim 1, namely trans-1-[3-(o-Methylphenyl)propyl]-2,5-dimethyl-4-(5-methyl-3-furoyl)piperazine hydrochloride.

23. The compound according to claim 1, namely trans-1-(3-Phenylpropyl)-2,5-dimethyl-4-(3-methyl-2-furoyl)piperazine hydrochloride.

24. The compound according to claim 1, namely trans-1-(3-Phenylpropyl)-2,5-dimethyl-4-(5-methyl-2-furoyl)piperazine hydrochloride.

25. The compound according to claim 1, namely trans-1-(3-Phenylpropyl)-2,5-dimethyl-4-(2-methyl-3-furoyl)piperazine hydrochloride.

26. The compound according to claim 1, namely 1-(3-Phenylpropyl)-3-methyl-4-(5-methyl-2-furoyl)-piperazine hydrochloride.

27. The compound according to claim 1, namely 1-(3-Phenylpropyl)-3-methyl-4-(3-methyl-2-furoyl)-piperazine hydrochloride.

28. The compound according to claim 1, namely 1-[3-(o-Methylphenyl)propyl]-3-methyl-4-(3-methyl-2-furoyl)piperazine hydrochloride.

* * * * *